United States Patent [19]
Chuter

[11] Patent Number: 5,725,547
[45] Date of Patent: Mar. 10, 1998

[54] CORRUGATED STENT

[76] Inventor: Timothy A. M. Chuter, 4263 Kerwood Ct., San Diego, Calif. 92130

[21] Appl. No.: 582,942

[22] Filed: Jan. 4, 1996

[51] Int. Cl.$^6$ .................................................. A61M 29/00
[52] U.S. Cl. ............................................ 606/194; 606/191
[58] Field of Search ................................... 606/191, 200; 623/1, 11, 12

[56] References Cited

U.S. PATENT DOCUMENTS

| | | |
|---|---|---|
| 4,503,569 | 3/1985 | Dotter . |
| 4,553,545 | 11/1985 | Maass . |
| 4,580,568 | 4/1986 | Gianturco . |
| 4,655,771 | 4/1987 | Wallsten . |
| 4,733,665 | 3/1988 | Palmaz . |
| 4,739,762 | 4/1988 | Palmaz . |
| 4,776,337 | 10/1988 | Palmaz ........................................ 623/1 |
| 4,820,298 | 4/1989 | Leveen et al. . |
| 4,830,003 | 5/1989 | Wolff et al. . |
| 4,886,062 | 12/1989 | Wiktor . |
| 4,913,141 | 4/1990 | Hillstead . |
| 4,990,155 | 2/1991 | Wilkoff . |
| 5,015,253 | 5/1991 | MacGregor . |
| 5,019,085 | 5/1991 | Hillstead . |
| 5,019,090 | 5/1991 | Pinchuk . |
| 5,037,427 | 8/1991 | Harada et al. . |
| 5,104,404 | 4/1992 | Wolff . |
| 5,133,732 | 7/1992 | Wiktor . |
| 5,135,536 | 8/1992 | Hillstead . |
| 5,222,971 | 6/1993 | Willard et al. . |
| 5,226,913 | 7/1993 | Pinchuk . |
| 5,316,023 | 5/1994 | Palmaz et al. . |
| 5,342,348 | 8/1994 | Kaplan . |
| 5,342,387 | 8/1994 | Summers . |
| 5,366,504 | 11/1994 | Andersen et al. . |
| 5,370,683 | 12/1994 | Fontaine . |
| 5,415,664 | 5/1995 | Pinchuk . |
| 5,474,563 | 12/1995 | Myler et al. . |
| 5,476,508 | 12/1995 | Amstrup ........................................ 623/1 |
| 5,507,767 | 4/1996 | Maeda et al. . |
| 5,514,154 | 5/1996 | Lau et al. . |
| 5,527,354 | 6/1996 | Fontaine et al. . |
| 5,540,712 | 7/1996 | Kleshinski et al. . |
| 5,571,170 | 11/1996 | Palmaz et al. . |
| 5,591,228 | 1/1997 | Edoga . |
| 5,603,721 | 2/1997 | Lau et al. . |
| 5,609,627 | 3/1997 | Coicoechea et al. . |
| 5,613,979 | 3/1997 | Trotta et al. . |
| 5,617,878 | 4/1997 | Taheri . |
| 5,628,782 | 5/1997 | Myers et al. . |
| 5,628,788 | 5/1997 | Pinchuk . |
| 5,630,829 | 5/1997 | Lauterjung . |
| 5,632,763 | 5/1997 | Glastra . |
| 5,645,532 | 7/1997 | Horgan . |
| 5,649,949 | 7/1997 | Wallace et al. . |
| 5,649,951 | 7/1997 | Davidson . |

OTHER PUBLICATIONS

Description of Hexstent by Applicant, T.A.M. Chuter.

*Primary Examiner*—Glenn K. Dawson
*Attorney, Agent, or Firm*—William G. Lane, Inc., P.C.

[57] ABSTRACT

The present invention concerns an improved corrugated stent which is designed to maximize expansion ratio, source of expansion, and flexibility, while minimizing the shortening which generally takes place with prior art stents which effect is achieved by alternating between transversely and longitudinally oriented limbs down the length of the stent.

11 Claims, 2 Drawing Sheets

CORRUGATED STENT

BACKGROUND OF THE INVENTION

The term "stent" is conventionally taken to mean an expandable framework that is used to support corporeal lumens. The primary structural elements of a stent (the limbs) are joined, or interwoven with one another to form a cylinder. Most stents expand by the movement of their limbs from a longitudinal orientation, in which they are parallel to the long axis of the stent lumen, to a more transverse orientation, in which they are more perpendicular to the long axis of the stent lumen.

A number of prior art references are available in the art, each of which references are directed to some specific discreet elements of the system which are described and claimed in the present invention, however, none of which is directed to the totality of the combination, or its use and function in the manner described and claimed herein.

The following prior art references are known to the inventor:

U.S. Pat. No. 4,580,568, which issued to Gianturco on Apr. 8, 1986, discloses an endovascular stent formed of stainless steel wire which is arranged in a closed zig-zag pattern.

U.S. Pat. No. 4,733,665, which issued to Palmaz on Mar. 29, 1988, relates to an expandable intraluminal vascular graft which is expanded within a blood vessel using an angioplasty balloon associated with a catheter.

U.S. Pat. No. 4,739,762, which issued to Palmaz on Apr. 26, 1988, teaches an expandable intraluminal graft for use within a body passageway or duct which is particularly useful for repairing blood vessels which have been narrowed or occluded by disease.

U.S. Pat. No. 4,830,003, which issued to Wolff et al on May 16, 1989, discloses a cylindrical shaped stent useful to prevent arterial acute closure which is formed of longitudinal wires of biocompatible material which wires have been welded together in pairs at alternate ends with each pair of wires bent into a V-section. The wires are formed into a cylinder which is welded closed in order to form the stent.

U.S. Pat. No. 5,104,404, which issued to Wolff on Apr. 14, 1992, teaches an intravascular stent which is applied within the peripheral or coronary arteries of a living animal or a human being in order to return patency after a balloon angioplasty. The stent taught in this reference is an articulated separate stent comprising at least two segments each of which segments have a generally tubular shape and a hinge means extending between and connecting adjoining stent segments.

U.S. Pat. No. 5,019,090, which issued to Pinchuk on May 28, 1991, relates to radially expandable stents which include a plurality of adjacent generally circumferential sections which are substantially axially positioned with respect to each other.

U.S. Pat. No. 4,886,062, which issued to Wiktor on Dec. 12, 1989, discloses a device which is to be used as a vascular stent comprising a cylindrical open ended wire made of a low memory metal, which is characterized by its ability to be expanded radially to a larger diameter after initial implantation, along with a means for causing said stent to expand to a larger diameter and a method for transporting, positioning and implantation of such stent.

U.S. Pat. No. 5,370,683, which issued to Fontaine on Dec. 6, 1994, is directed to a vascular stent for reducing hemodynamic disturbances caused by angioplasty, said stent being formed from a single filament of low memory biocompatible material having a series of U-shaped bends. The filament is wrapped about a mandril in a circular fashion in order to align the curved portions of each bend which may then be connected.

U.S. Pat. No. 5,226,913, which issued to Pinchuk on Jul. 13, 1993, teaches a radially expandable stent which includes a plurality of adjacent generally circumferential sections that are substantially axially positioned with respect to each other, wherein at least one of the generally circumferential sections has an expandable segment which imparts a circumferential and radial expandability to the stent.

U.S. Pat. No. 4,913,141, which issued to Hillstead on Apr. 3, 1990, relates to a stent delivery system for routing the stent to a defined position within a subject's blood vessel.

U.S. Pat. No. 5,133,732, which issued to Wiktor on Jul. 28, 1992, discloses a stent for implantation into a body vessel comprising a cylindrical stent body which has been coiled from a generally continuous wire which has been imparted with a deformable zig-zag structure.

U.S. Pat. No. 5,135,536, which issued to Hillstead on Aug. 4, 1994, is directed to a stent for reinforcing a vessel wall which is constructed from a single elongated wire. The wire has been first bent into a series of tight bends and then rolled around a mandrel in order to create junctions of wire which are permanently adhered. The completed stent forms a cylindrical shape which can be expanded from its initial diameter to a larger implanted diameter by the application of radial outward force from a balloon catheter.

U.S. Pat. No. 4,655,771, which issued to Wallsten on Apr. 7, 1987, teaches a prosthesis for transluminal implantation comprising a flexible tubular body which has a diameter that is variable by axial movement of the ends of the body relative to each other and which is composed of several individual rigid but flexible thread elements each of which extends in helix configuration with the centerline of the body as a common axis.

U.S. Pat. No. 5,015,253, which issued to MacGregor on May 14, 1991, discloses a generally tubular stent that includes a non-woven structure formed by two or more generally helically shaped cylinders of stiff strand material where the strand material forming the non-woven structure is preferably secured together at attachment sites which allow the stent to be flexible and adjustable to meet various needs.

As noted, the U.S. Pat. No. 4,655,771 refers to a stent comprised of helical limbs. This stent (known as a Wallstent), and others like it, have no joints between adjacent limbs. The structural stability of the stent is achieved by interlocking of the limbs in the braided construction. Stent expansion is therefore achieved without deformation of any junctional area. This feature is responsible for the principal advantages of this stent, those being; first, stress tends to be spread throughout the limb, and second, the limbs can be tightly packed, since there are no bulky junctions. However, the lack of junctional deformation is also the principal disadvantage. The limbs of a Wallstent deform very little as stent diameter changes. Therefore, very little energy is stored in the collapsed stent and expansion tends to be weak.

The flexibility and compliance of any expanded stent depend on the angular orientation of the limbs. Transversely oriented limbs impart low compliance and high flexibility, which are both desirable features. However, to reach this state, the stent must shorten markedly during expansion, which is undesirable. The Wallstent is no exception to these rules.

The current invention maximizes expansion ratio, force of expansion, and flexibility, while minimizing shortening, and compliance by alternating between transversely and longitudinally oriented sections in the limbs that extend down the length of the stent.

It is, therefore, an object of the present invention to provide for an improved stent which has been designed to maximize expansion ratio over available prior art stents.

It is a further object of the present invention to provide for an improved stent which incorporates an enhanced source of expansion over available prior art stents.

It is yet another object of the present invention to provide for an improved stent which exhibits enhanced flexibility over available prior art stents and, Lastly, it is an object of the present invention to provide for an improved stent which is designed to maximize expansion force by providing an enhanced source of expansion and providing enhanced flexibility, while minimizing the shortening effect which is generally exhibited by available prior art stents.

These and other objects of the invention will become apparent from the following discussion of the invention.

SUMMARY OF THE INVENTION

The present invention provides for an improved stent which is designed to maximize expansion ratio, source of expansion and flexibility while minimizing the shortening which generally takes place with prior art stents which effect is achieved by alternating between transversely and longitudinally oriented sections in the limbs down the length of the stent.

The construction and obvious advantages of the system provided for by the present invention will be more clearly understood from the following description of the various specific embodiments when read in conjunction with the accompanying drawings.

DETAILED DESCRIPTION OF THE INVENTION

Figure 1:
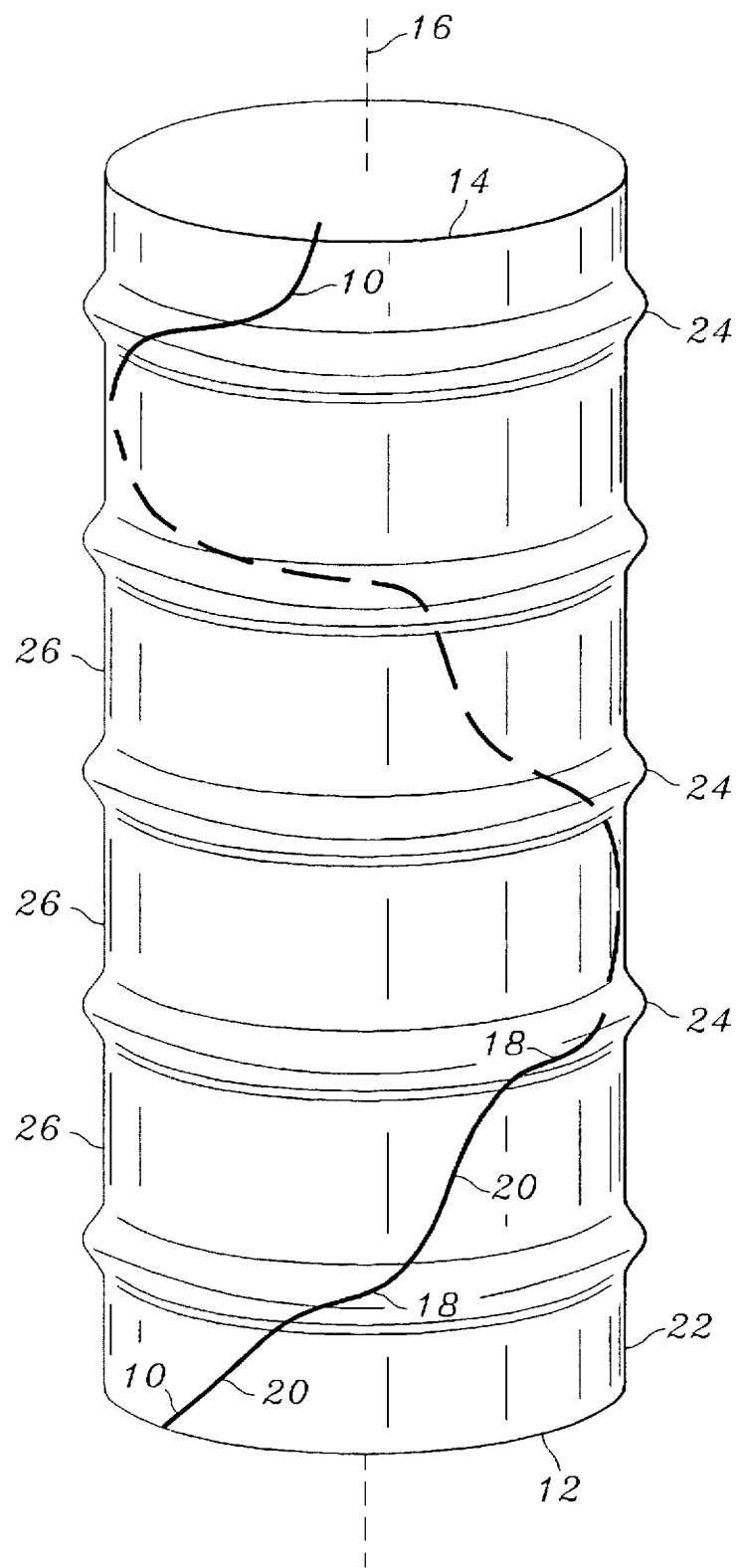
FIG. 1 is a schematic representation of a stent of the present invention showing one of the multiplicity of individual limbs within a schematic representation of the outer envelope of the stent which is formed by the intertwining of a number of said limbs.

The present invention is directed to an improved stent which is designed to maximize expansion ratio, source of expansion, and flexibility, while minimizing the shortening which generally takes place with prior art stents which effect is achieved by alternating between transversely and longitudinally oriented sections in the limbs down the length of the stent.

The novel stent of the present invention, like the Wallstent, is a cylinder formed by the braiding of a multiplicity of springy wires or stent limbs. The spacing and thickness of the stent limbs is dependent upon the desired diameter of the stent and mechanical properties, such as the compliance, which are dictated by the end use. Each of the individual limbs of the novel stent of the present invention spiral from one end of the stent to the other. However, unlike the Wallstent and other prior art stents, these limbs do not have a uniform orientation relative to the long axis of the stent, but rather bend back and forth as will be apparent from the schematic representation of FIG. 1. Consequently, the angle between the long axis of the limb and the long axis of the stent lumen is not constant, for any given stent diameter. Periodic variations in the orientation of one limb correspond to the variations in the orientation of all the other individual limbs at that level. At any particular level, all the limbs are at the same angle to the long axis. As the angle varies so do the mechanical properties of the stent, such as compliance, and flexibility. Therefore, these properties will alternate from one level to the next, forming a series of rings. Rings of transversely oriented sections of each limb are more flexible and more resistant to compressive loading, but they shorten markedly during stent expansion. Rings of longitudinally oriented sections of each limb are less flexible and resistant to compression, but they shorten little during stent expansion. Since this stent contains alternating rings of both types, it has the properties of both. Even though the rings of transversely oriented limbs are few and widely spaced, they still confer great resistance to compression and moderate flexibility. In this regard, they can be likened to the tracheal cartilages.

A second property, which is conferred by the undulating bends in the individual limbs, is the additional force needed to straighten the limb in order to compress the stent. The additional energy produces much more forcible stent expansion. As a result, the stent of the present invention can be constructed of finer, more widely spaced wires than a corresponding prior art stent formed of unbent wires.

A third effect exhibited by the stent of the present invention is corrugation of the stent surface. With the stent in its expanded state, the character of the rings formed by the transversely oriented sections of each of the individual limbs are wider than the rings formed by the longitudinally oriented sections of these limbs. The extent of variation from one diameter to the next depends on the periodicity of the bends in the stent limbs and the degree of bending. Bends occurring at narrow intervals produce fine, closely spaced corrugations, which are preferable in most applications. The corrugation which results in the surface of the stent helps fix the stent to the arterial wall, preventing stent migration. The corrugated stent of the present invention is also more resistant to compressive loading.

Figure 2:
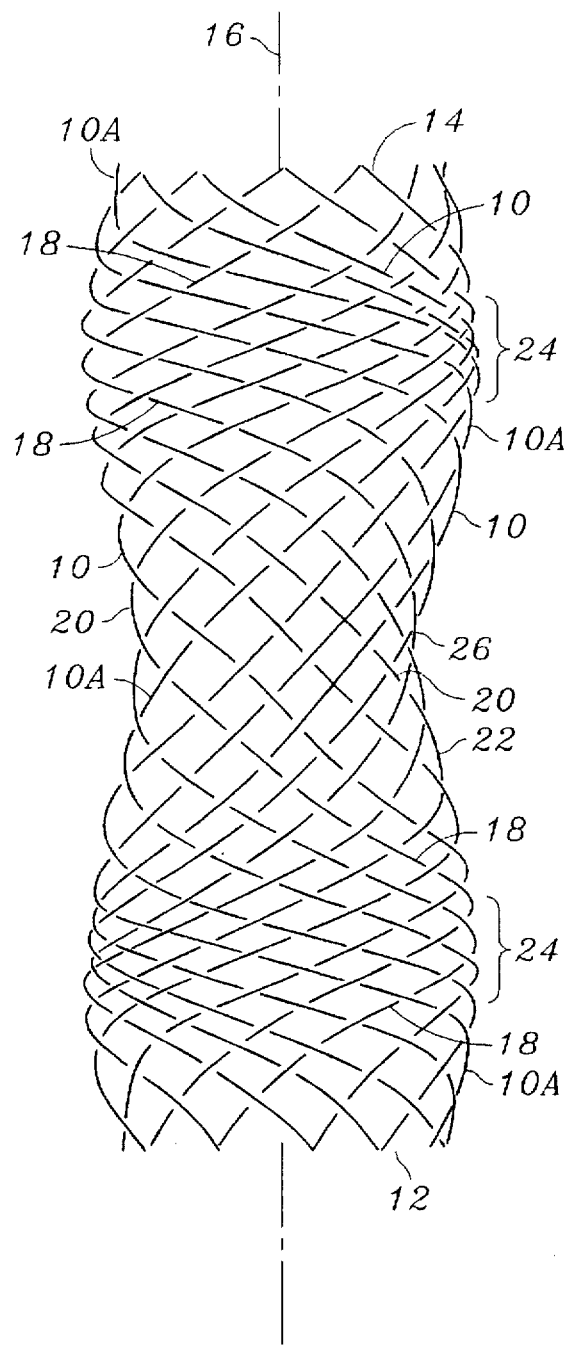
FIG. 2 is a schematic representation of a stent of the present invention showing a multiplicity of individual limbs within a schematic representation of the outer envelope of the stent which is formed by the intertwining of a number of said limbs.
Figure 3:
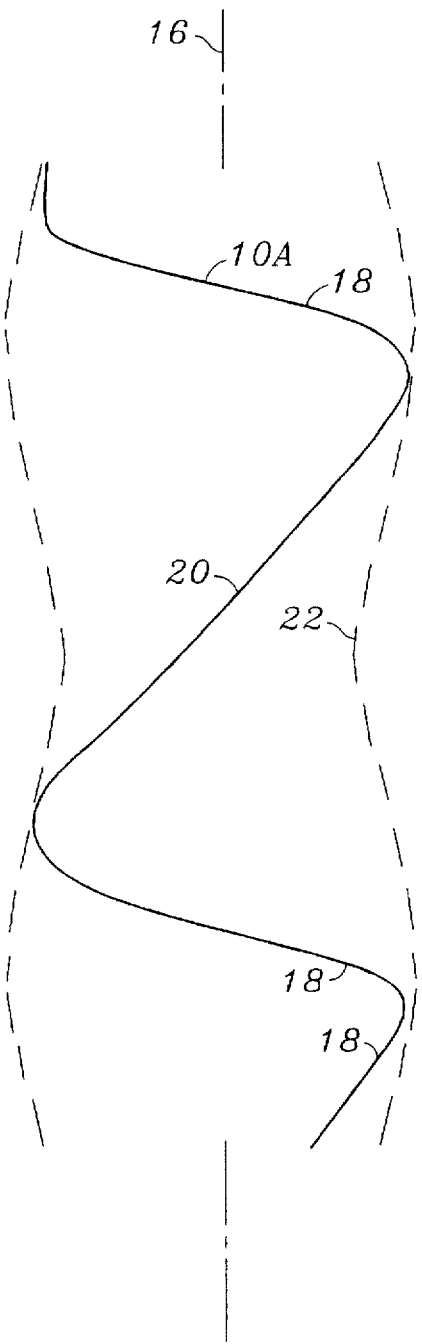
FIG. 3 is a schematic representation of the stent of FIG. 2 showing one of the multiplicity of individual limbs within a schematic representation of the outer envelope of the stent.

With reference to FIGS. 1, 2, and 3, a schematic representation of a stent of the present invention showing one of the multiplicity of individual limbs within a schematic representation of the outer envelope of the stent which is formed by the intertwining of a number of said limbs is depicted. One of a multiplicity of individual stent limbs (10) is shown which extends from lower end (12) of the stent envelope to the upper end (14) of the stent envelope. The individual stent limb (10) spirals around the longitudinal axis (16) of the stent in an undulating fashion generally defined by transversely oriented sections (18) and longitudinally oriented sections (20). The outer envelope (22) of the stent formed by the intertwining of a multiplicity of individual stent limbs identical in configuration to that shown will define a series of rings of transversely oriented sections (24) and longitudinally oriented sections (26) which will have varying diameters depending upon the periocity of such bends in the stent limbs and the degree of bending therein.

It will be appreciated that each of the individual stent limbs as defined in FIG. 1 will be constructed of a suitable biocompatible springy wire material. Further, it will be appreciated that each of the individual stent limbs will be formed of a wire material which may vary in thickness depending upon the particular end characteristics required. The number of individual stent limbs may vary widely depending upon the specific end use to which the resultant stent will be put.

The overall characteristics of the resultant stent formed by the intertwining of a multiplicity of stent limbs such as that depicted in FIGS. 1, 2, and 3 will be determined by a combination of the choice of particular biocompatible materials of which the individual stent limbs are made, the number of stent limbs employed in forming the stent, the overall thickness of the wire utilized to form each stent limb and the periodicity and degree of bending incorporated in each such stent limb.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

I claim:

1. An improved stent having a corrugated stent envelope which is designed to maximize the expansion ratio, source of expansion, flexibility, and resistance to compressive forces while minimizing shortening and compliance, comprising a multiplicity of intertwining individual stent limbs which define a stent envelope, each stent limb extending from one end of the stent to the other, each stent limb spiraling around the long axis of the stent, each stent limb continuously bending to form a series of alternating transversely oriented sections and longitudinally oriented sections running the length of the stent limb, all the stent limbs having the same configuration, the stent envelope having alternating first and second rings forming the corrugated stent envelope and running the length of the stent, the first rings corresponding to the transversely oriented sections of the stent limbs, and the second rings corresponding to the longitudinally oriented sections of the stent limbs, the stent envelope at each first ring of the stent having a greater diameter than at the adjacent second rings.

2. The improved stent according to claim 1 wherein the first rings are comparatively more flexible and more resistant to compression than the second rings.

3. The improved stent according to claim 1 wherein the first rings are widely spaced apart.

4. The improved stent according to claim 1 wherein the first rings are relatively narrow.

5. The improved stent according to claim 1 wherein the series of alternating transversely and longitudinally oriented sections of the stent limbs occur at narrow intervals.

6. The improved stent according to claim 1 wherein the stent limbs are formed from biocompatible springy wire material.

7. An improved stent having a corrugated stent envelope which is designed to maximize the expansion ratio, source of expansion, flexibility, and resistant to compressive forces while minimizing shortening and compliance, comprising a multiplicity of intertwining individual stent limbs which define the stent envelope, each stent limb extending from one end of the stent to the other, each stent limb comprising a series of alternating transversely oriented sections and longitudinally oriented sections running the length of the stent limb, each stent limb spiraling around the longitudinal axis of the stent in an undulating fashion defined by the transversely oriented sections and the longitudinally oriented sections of the stent limb, all the stent limbs having the same configuration, the angle between the long axis of each stent limb and the longitudinal axis of the stent varying along the length of the stent, the stent envelope having alternating first and second rings forming the corrugated stent envelope and running the length of the stent, the first rings corresponding to the transversely oriented sections of the stent limbs and the second rings corresponding to the longitudinally oriented sections of the stent limbs, the stent envelope at each first ring of the stent having a greater diameter than at the adjacent second rings.

8. The improved stent according to claim 7 wherein the first rings are comparatively more flexible and more resistant to compression than the second rings.

9. The improved stent according to claim 7 wherein the first rings are widely spaced apart.

10. The improved stent according to claim 7 wherein the first rings are relatively narrow.

11. The improved stent according to claim 7 wherein the series of alternating transversely and longitudinally oriented sections of the stent limbs occur at narrow intervals.

* * * * *